United States Patent [19]
O'Neil et al.

[11] Patent Number: 6,010,534
[45] Date of Patent: *Jan. 4, 2000

[54] ROTATABLE TIBIAL PROSTHESIS WITH KEYED AXIAL SECUREMENT

[75] Inventors: Michael J. O'Neil, West Barnstable; Arnold Oyola, Taunton; Edward J. Cheal, Duxbury, all of Mass.

[73] Assignee: Johnson & Johnson Professional, Inc., Raynham, Mass.

[ * ] Notice: This patent is subject to a terminal disclaimer.

[21] Appl. No.: 08/937,965

[22] Filed: Sep. 25, 1997

[51] Int. Cl.⁷ ........................................................ A61F 2/38
[52] U.S. Cl. ................................................. 623/20; 623/18
[58] Field of Search .................................... 623/16, 18, 20, 623/22

[56] References Cited

U.S. PATENT DOCUMENTS

| | | |
|---|---|---|
| 4,136,405 | 1/1979 | Pastride et al. ............................ 623/20 |
| 4,219,893 | 9/1980 | Noiles ...................................... 3/1.911 |
| 4,301,553 | 11/1981 | Noiles ...................................... 3/1.911 |
| 4,538,305 | 9/1985 | Engelbrecht et al. .................... 623/20 |
| 4,790,853 | 12/1988 | Engelbrecht et al. .................... 623/20 |
| 4,888,021 | 12/1989 | Forte et al. ............................... 623/20 |
| 4,950,297 | 8/1990 | Elloy et al. ............................... 623/20 |
| 5,011,496 | 4/1991 | Forte et al. ............................... 623/20 |
| 5,026,399 | 6/1991 | Engelbrecht et al. .................... 623/18 |
| 5,059,216 | 10/1991 | Winters .................................... 623/20 |
| 5,071,438 | 12/1991 | Jones et al. ............................... 623/20 |
| 5,080,675 | 1/1992 | Lawes et al. ............................. 623/20 |
| 5,171,283 | 12/1992 | Pappas et al. ............................ 623/20 |
| 5,370,699 | 12/1994 | Hood et al. ............................... 623/20 |
| 5,370,701 | 12/1994 | Finn ........................................ 623/20 |

(List continued on next page.)

FOREIGN PATENT DOCUMENTS

| | | |
|---|---|---|
| 0018364 | 11/1980 | European Pat. Off. .......... A61F 1/00 |
| 0046926 | 3/1982 | European Pat. Off. .......... A61F 1/03 |
| 0183670 | 6/1986 | European Pat. Off. .......... A61F 2/38 |
| 0346183 | 12/1989 | European Pat. Off. .......... A61F 2/38 |
| 0519872 | 12/1992 | European Pat. Off. .......... A61F 2/38 |
| 0529408 | 3/1993 | European Pat. Off. .......... A61F 2/38 |
| 0568756 | 11/1993 | European Pat. Off. .......... A61F 2/38 |
| 0592750 | 4/1994 | European Pat. Off. .......... A61F 2/38 |
| 0626156 | 11/1994 | European Pat. Off. .......... A61F 2/38 |
| 0627202 | 12/1994 | European Pat. Off. .......... A61F 2/38 |
| 0636353 | 2/1995 | European Pat. Off. .......... A61F 2/38 |
| 0678286 | 10/1995 | European Pat. Off. .......... A61F 2/38 |
| 0682925 | 11/1995 | European Pat. Off. .......... A61F 2/38 |
| 732091 | 9/1996 | European Pat. Off. ................. 623/20 |
| 2726174 | 5/1996 | France ............................. A61F 2/38 |
| 2728782 | 7/1996 | France ............................. A61F 2/38 |
| 3136636 | 3/1983 | Germany ........................ A61F 1/03 |
| 9517860 | 7/1995 | WIPO .............................. A61F 2/38 |
| 9525484 | 9/1995 | WIPO .............................. A61F 2/38 |
| 9530390 | 11/1995 | WIPO .............................. A61F 2/38 |
| WO9600538 | 1/1996 | WIPO .............................. A61F 2/38 |
| 9603097 | 2/1996 | WIPO .............................. A61F 2/38 |

OTHER PUBLICATIONS

DePuy®, LCS AP Glide™, Clinical Evaluation, May 1995, 11 pp.

*Primary Examiner*—David H. Willse
*Assistant Examiner*—Bruce E. Snow
*Attorney, Agent, or Firm*—Nutter, McClennen & Fish, LLP

[57] ABSTRACT

A joint prosthesis system includes first and second components that are joinable to one another in a manner to permit axial rotation of one component relative to the other component while achieving axial securement of the two components. In one embodiment the joint prosthesis system is a knee joint prosthesis and the two components are a tibial tray and a tibial bearing insert. The tibial bearing insert includes a mating stem that has one or more positive surface features on its exterior surface. The positive surface features mate with axial slot(s) formed in a mating cavity of the tibial tray to enable insertion of the mating stem within the mating cavity. Upon insertion the positive surface features are engaged by a circumferential groove disposed distally of the axial slot(s). Misalignment of the positive surface features and the axial slot(s) enables proper orientation of the tibial tray and tibial bearing insert, and provides axial securement of the two components.

22 Claims, 3 Drawing Sheets

U.S. PATENT DOCUMENTS

| | | | |
|---|---|---|---|
| 5,387,240 | 2/1995 | Pottenger et al. | 623/20 |
| 5,395,401 | 3/1995 | Baher | 623/20 |
| 5,413,608 | 5/1995 | Keller | 623/20 |
| 5,489,311 | 2/1996 | Cipolletti | 623/20 |
| 5,683,468 | 11/1997 | Pappas | 623/20 |
| 5,755,801 | 5/1998 | Walker et al. | 623/20 |
| 5,871,543 | 2/1999 | Hofmann | 623/20 |

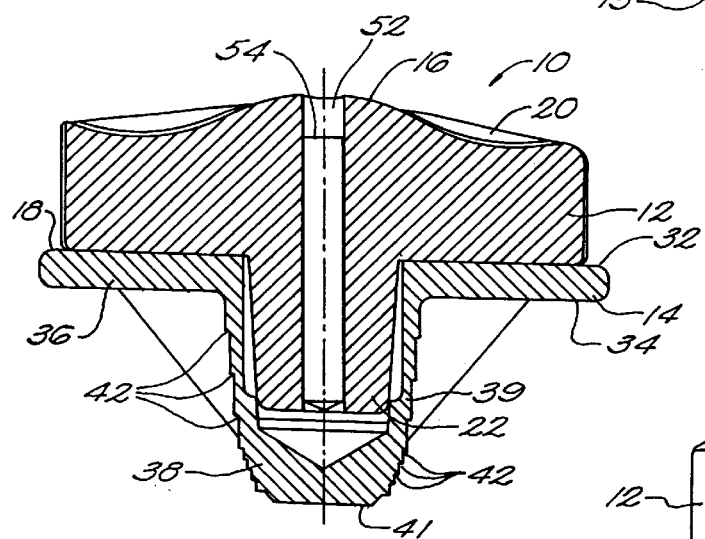
FIG. 1
FIG. 2
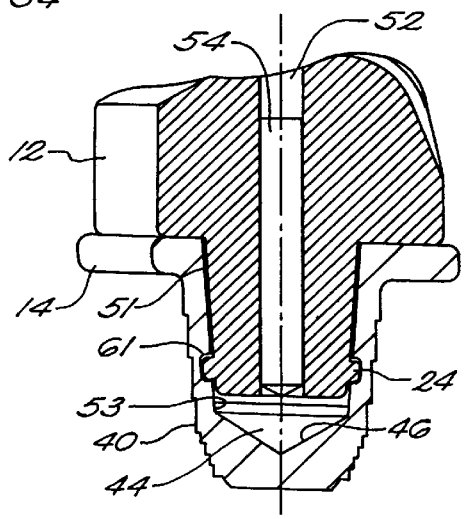
FIG. 3
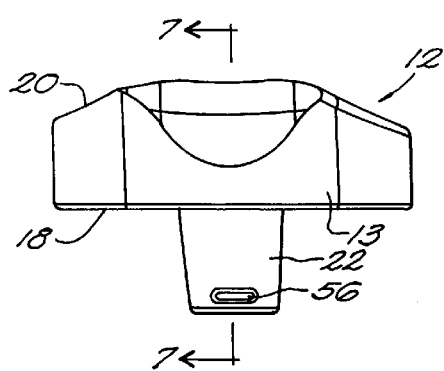
FIG. 5
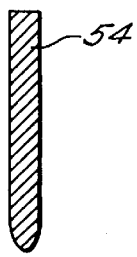
FIG. 4

ROTATABLE TIBIAL PROSTHESIS WITH KEYED AXIAL SECUREMENT

CROSS REFERENCE TO RELATED APPLICATIONS

Not applicable.

STATEMENT REGARDING FEDERALLY SPONSORED RESEARCH

Not applicable.

BACKGROUND OF THE INVENTION

The invention relates to knee joint prostheses and more particularly to tibial components of knee joint prostheses that feature a tibial bearing insert that is rotatable with respect to a tibial tray upon which it is mounted.

Joint replacement surgery is quite common and enables many individuals to function normally when otherwise it would not be possible to do so. Artificial joints are normally composed of metallic, ceramic and/or plastic components that are fixed to existing bone.

Knee arthoplasty is a well known surgical procedure by which a diseased and/or damaged natural knee joint is replaced with a prosthetic knee joint. Typical knee prostheses include a femoral component, a patella component, a tibial tray or plateau, and a tibial bearing insert. The femoral component generally includes a pair of laterally spaced apart condylar portions, the distal surfaces of which articulate with complementary condylar elements formed in a tibial bearing insert.

The tibial tray is mounted within the tibia of a patient. Typically, the tibial bearing insert, which is usually made of ultra high molecular weight polyethylene (UHMWPE) is mounted upon the superior surface of the tibial tray. Load and stress are placed upon the knee prosthesis, and particularly on the tibial bearing insert, during normal daily use. These forces may lead to the displacement or dislocation of the insert from the tibial tray. To accommodate these forces, and to reduce the chances for dislocation, some tibial components of knee prostheses have been designed to allow rotation of the tibial bearing insert relative to the proximal or superior surface of the tibial tray, about the longitudinal axis of the prosthesis. Such rotation, when controlled, can increase the contact area between the femoral condyles and the tibial bearing insert throughout the range of knee motion, thus reducing stress on the tibial bearing insert.

Some knee prosthesis tibial components accommodate insert rotation without providing axial securement of the tibial bearing insert within the tibial tray. That is, some tibial bearing inserts that are able to rotate with respect to a tibial tray are not fully secured within the tibial tray. Certain forces to which the knee is subjected, particularly forces with axially directed components, may cause the tibial bearing insert to separate from the tibial tray.

Various designs for rotatable tibial components of knee joint prostheses are known in the art. For example, U.S. Pat. No. 4,219,893 (Noiles) and U.S. Pat. No. 4,301,553 (Noiles) disclose knee joint prostheses in which the tibial component comprises a tibial tray having a bearing surface with a recessed region within which the tibial bearing insert may rest. A sufficient clearance is provided in the bearing surface of the tibial tray to allow some medial-lateral rotation of the tibial bearing insert with respect to the tray. Other patents that disclose tibial components of knee joint prostheses in which a tibial bearing insert is rotatable with respect to the tibial tray are disclosed in U.S. Pat. Nos. 5,059,216 (Winters); 5,071,438 (Jones et al); 5,171,283 (Pappas et al); and 5,489,311 (Cipolletti).

Despite the existing designs for knee joint prostheses having a rotatable tibial component, there remains a need for prostheses that allow rotation of the tibial bearing insert to accommodate the stresses placed upon the knee. At the same time, such tibial bearing inserts should possess sufficient axial securement so as to decrease or eliminate the possibility of subluxation of the tibial bearing insert.

SUMMARY OF THE INVENTION

The invention relates to a joint prosthesis system in which one component of the prothesis system has rotational capability. In a preferred embodiment, the joint prosthesis is a tibial component of a knee joint prothesis, and the tibial bearing insert is rotatable. The tibial component design of the invention permits some rotation of the tibial bearing insert relative to the proximal or superior surface of the tibial tray, while maintaining axial securement of the tibial bearing insert to the tibial tray and to the patient's tibia. The term "axial securement" refers to the ability of the tibial bearing insert to resist withdrawal or separation from the tibial tray when subjected to a separation force.

The prothesis system of the invention comprises a first component (e.g., a tibial tray) having a superior mounting surface and an inferior bone contacting surface. The bone contacting surface includes an anchor stem having outer, implantable side and distal walls. Preferably, a cavity is formed in the mounting surface and extends into the anchor stem. This cavity is defined by inner side and distal walls of the anchor stem.

A second component of the prothesis system (e.g., a tibial bearing insert) has a superior articulation surface and an inferior surface that is mountable upon the mounting surface of the first component. The inferior surface includes a mating stem that is mountable within the cavity of the first component and which has a size and shape complementary to the cavity.

The prothesis system also includes a selectively engagable locking mechanism that includes at least one nondeformable positive surface feature on one of the mating stem and the interior walls of the cavity and at least one cooperating negative surface feature on the other of the mating stem and the internal wall of the cavity. The locking mechanism is effective, when it is engaged, to allow the second component to rotate in the medial-lateral plane relative to the first component, while at the same time axially securing the second component to the first component.

Preferably, the locking mechanism is in the form of a bayonet-type locking system. That is, at least one axial slot is formed in the interior side wall of the cavity. This axial slot communicates with a circumferential groove that is formed in the cavity distally of the axial slot. At least one positive surface feature protrudes from the exterior side wall of the mating stem. The positive surface feature has dimensions that are sufficient to permit the mating stem to fit within the cavity only when it is aligned with the axial slot. When the positive surface feature and the axial slot are aligned, the second component is fully inserted within the first component and the positive surface feature is engaged within the circumferential groove. Rotation of the first component relative to the second component, to properly orient the two components, causes the positive surface feature to travel within the circumferential groove and to become misaligned with the axial slot, thereby creating positive axial securement of the second component with the first component.

In one embodiment the prosthesis system includes an axial bore formed in the superior surface of the second component and extending into the mating stem of the second component. The bore has a size and dimensions sufficient to receive an elongate reinforcement pin that can be mounted within the bore.

BRIEF DESCRIPTION OF THE DRAWINGS

FIG. 1 is a top view, partially cut away, of a tibial component of a knee joint prosthesis system constructed according to the present invention.

FIG. 2 is a sectional view at lines 2—2 of the prosthesis system shown in FIG. 1.

FIG. 3 is a sectional view at lines 3—3 of the joint prosthesis system shown in FIG. 1.

FIG. 4 is a sectional view of a reinforcement pin useful with the joint prosthesis system of FIG. 1.

FIG. 5 is a front view of a tibial bearing insert shown in the joint prosthesis system of FIG. 1.

DETAILED DESCRIPTION OF THE INVENTION

Figure 7:
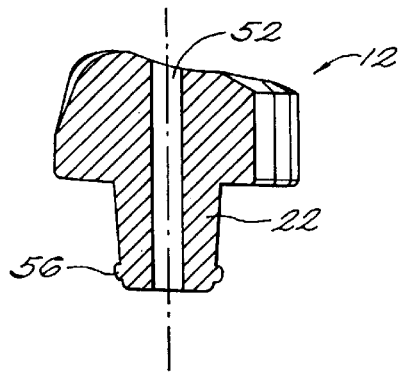
FIG. 7 is a sectional view at lines 7—7 of the tibial bearing insert shown in FIG. 5.

The invention provides a prosthesis system 10 that has first and second components that can be axially secured to one another while maintaining the ability of one component to rotate with respect to the other. For purposes of illustration the system 10 is shown as the tibial component of a knee joint prosthesis. It is understood, however, that the invention is applicable to other prostheses.

Referring to FIGS. 1–4, the system 10 includes a first component in the form of a tibial tray 14, upon which is mounted a second component, i.e., tibial bearing insert 12. The mounting of the tibial bearing insert 12 to the tibial tray 14 is such that the tibial bearing insert is able to rotate with respect to the proximal or superior surface 32 of the tibial tray while remaining axially secured to the tibial tray.

The tibial bearing insert 12 has an anterior side 13, a posterior side 15, a superior articulation surface 16 and an inferior mating surface 18. The superior surface 16 may have one or more condylar elements 20 that are adapted to articulate with complementary condyle(s) of a femoral component (not shown) of a knee joint prosthesis. The inferior surface preferably includes a mating stem 22 that protrudes from the inferior mating surface 18 and that is adapted to mate selectively with tibial tray 14.

The tibial tray 14 includes an anterior side 17, a posterior side 19, a superior mating surface 32 and an inferior bone contacting surface 34. The bone contacting surface 34 has a first portion 36 that represents an area of the inferior surface that mounts upon the proximal surface of a resected tibia (not shown). A second portion 38 of the bone contacting surface 34 extends from the first portion 36 and is adapted to extend into a cavity (not shown) formed within a patient's tibia. Preferably, the second portion 38 is an elongate tibial stem 39 that extends from the first portion 36. The tibial stem 39 has outer side and distal walls 40, 41. The outer side walls 40 of the tibial stem 39 may have irregular surface features (such as steps 42) to enhance bone fixation.

The superior surface 32 of the tibial tray 14 includes an aperture 72 (which may be any suitable shape, e.g., substantially circular) that communicates with a mating cavity 44. The mating cavity 44 preferably is a blind cavity, defined by interior side walls 45, that extend into the tibial stem. The mating cavity 44 preferably terminates in an interior distal wall 46 that may be substantially cone-shaped, or of another shape suitable to accept a tibial stem.

The mating stem 22 of the tibial bearing insert 12 is adapted to fit within the mating cavity 44 of the tibial tray. A locking mechanism ensures that the mating stem 22 is secured within the mating cavity 44 in such a way that the tibial bearing insert is axially secured to the tibial tray. Moreover, the tibial bearing insert must be able to rotate relative to the tibial tray while the two components are secured to one another.

One of ordinary skill in the art will readily appreciate that the dimensions of cavity 44 and mating stem 22 may vary. In one embodiment the cavity 44 has a diameter that tapers from proximal 51 to distal 53 ends thereof at an angle in the range of about 0.25° to 5°. The diameter at the proximal end 51 is in the range of about 5 to 40 mm and the diameter at the distal end 53 is in the range of about 3 to 39 mm. The cavity 44 preferably has a depth in the range of about 5 to 75 mm.

The mating stem 22 should have a size and shape complementary to the cavity 44. Accordingly, the diameter of stem 22 should taper from about 6 to 38 mm at a proximal end to about 3 to 30 mm a distal end. The length of stem 22 preferably is in the range of about 4 to 75 mm.

The superior surface 16 of the tibial bearing insert 12 may optionally include a blind bore 52. The blind bore 52 is preferably substantially centrally located and is of a size and shape sufficient to receive a reinforcement pin 54 of the type shown in FIG. 4. Such reinforcement pins are well known in the art and may be substantially cylindrically shaped and made of a metal or metal alloy. Such pins may also have knurled or grooved surface features (not shown) as is known in the art. In one embodiment bore 52 is cylindrical, having a diameter of about 1 to 12 mm and a depth of about 5 to 75 mm.

The locking mechanism preferably is a bayonet-type locking mechanism that includes a non-deformable positive surface feature on one of the first or second components 12, 14 to be engaged within a locking channel formed within the other of the first or second components 12, 14. Preferably at least one access channel, which leads to the locking channel, is formed within the component. The access channel provides a means by which the positive surface feature may enter the locking channel. Rotation of the component with the positive surface feature causes the positive surface feature to become misaligned with the access channel so that one of the first or second components 12, 14 is positively engaged within the other of the first or second components 12, 14.

For purposes of illustration, the tibial bearing insert 12 is shown to be the component having a non-deformable positive surface feature 24 formed on the mating stem 22. At least one positive surface feature 24 is located on the mating stem 22. Preferably, at least two positive surface features are present on the stem. As illustrated in FIGS. 3 and 5 through 7 the positive surface features 24 are opposite each other on anterior and posterior sides 13, 15 of the lower portion of mating stem 22. Preferably the positive surface features 24 protrude from the side wall 30 of the mating stem 22 by a distance in the range of about 0.25 to 8 mm.

Figure 6:
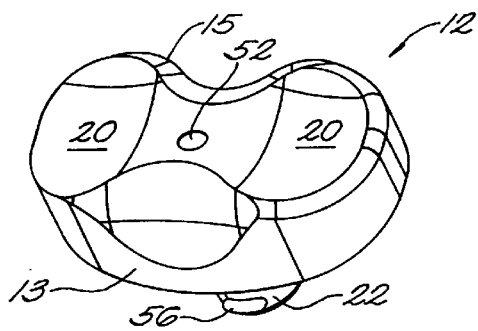
FIG. 6 is a perspective view of the tibial bearing insert of FIG. 5.
Figure 8:
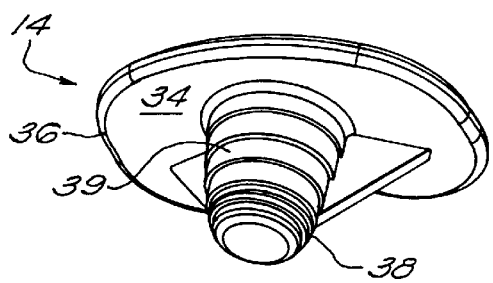
FIG. 8 is a perspective view of a tibial tray component of the joint prosthesis system shown in FIG. 1.
Figure 14:
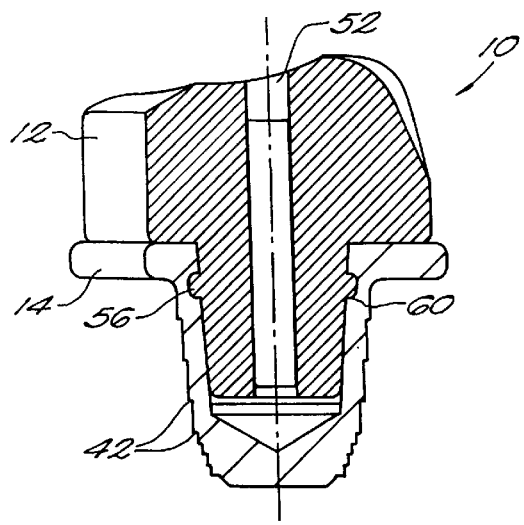
FIG. 14 is a sectional view of the tibial component of FIG. 13 at Lines 14—14.
Figure 13:
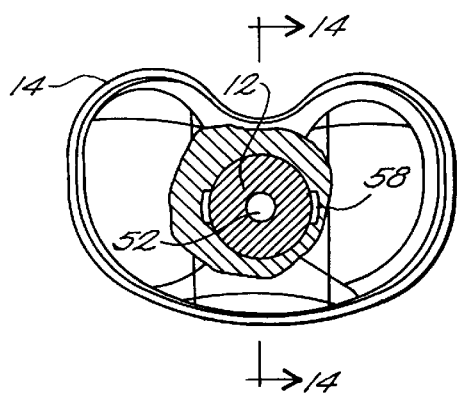
FIG. 13 is a top view, partially cut away, of a tibial component of a joint prosthesis system according to another embodiment of invention.

FIGS. 5 through 7 and 9 illustrate an embodiment of the invention in which a positive surface 24 feature is formed on the mating stem 22 of the tibial bearing insert 12 and negative surface features are formed within the mating cavity 44 of the tibial tray. As illustrated, the positive surface feature can be in the form of a raised knob 56 that is formed on anterior and posterior sides 3, 15 of the mating stem 22. The knobs 56 can be substantially rectangularly-shaped, although one of ordinary skill in the art will readily appreciate that other shapes may be employed as well. The knobs protrude from the exterior wall of the mating stem by about 0.25 to 8 mm. The knobs 56 may be located on a bottom portion of the mating stem, as shown in FIGS. 6 and 7, at a top portion of the mating stem as shown in FIG. 14, or at intermediate positions.

The non-deformable positive surface features 24 on the mating stem 22 protrude from the wall of the mating stem 22 to the extent that they prevent the mating stem from being inserted within the mating cavity 44 except through the negative surface features, as discussed below. The other dimensions of the positive surface features are not critical and can be readily determined by one of ordinary skill in the art.

The mating cavity 44 includes negative surface features that cooperate to allow the mating stem 22 to be inserted within the mating cavity and to be secured therein. In one embodiment the mating cavity includes opposed axial slots 58 that are formed in side wall 45 of mating cavity 44. Axial slots 58 form access channels that enable the mating stem 22 to be inserted within mating cavity 44. Preferably axial slots 58 are of a sufficient depth to receive the knobs 56 of the mating stem. Further, the axial slots 58 should be of a width that enables receipt of the knobs 56, while preventing any significant rotational movement of the knobs 56 when disposed within the axial slots 58. In an embodiment in which the knobs 56 are mounted on opposed anterior and posterior surfaces of the mating stem 22, the axially oriented slots 58 are disposed on opposed medial and lateral sides of the mating cavity. One of ordinary skill in the art can readily determine other suitable placement locations for the knobs 56 and the axial slots 58.

Figure 9:
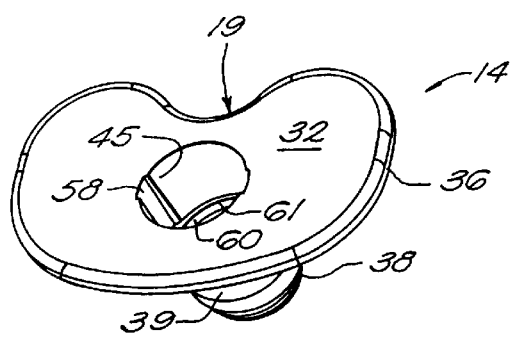
FIG. 9 is a perspective view of the tibial tray component of a knee joint prosthesis system shown in FIG. 1.
Figure 10:
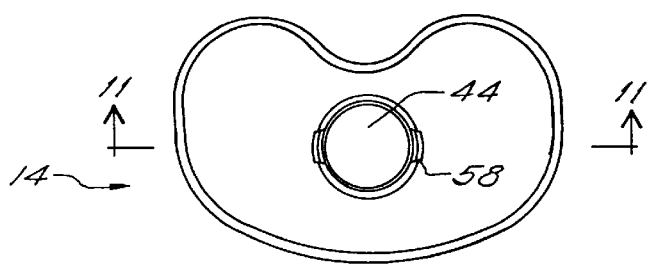
FIG. 10 is a top view of a tibial tray component of the knee joint prosthesis shown in FIG. 1.
Figure 11:
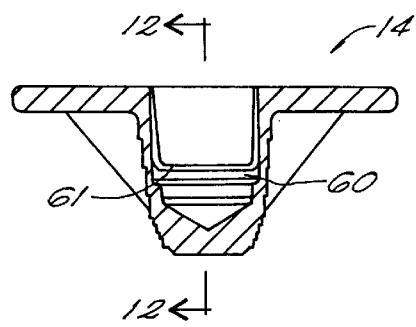
FIG. 11 is a sectional view of the tibial tray component of FIG. 10 at Lines 11—11.
Figure 12:
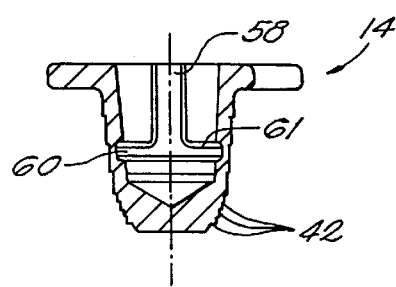
FIG. 12 is a sectional view of the tibial tray component of FIG. 11 at Lines 12—12.

As shown in FIGS. 1, 3 and 9, the axial slots 58 terminate distally at a circumferential groove 60 which serves as a locking channel. Circumferential groove 60, like axial slot 58, has dimensions that are sufficient to receive the knobs 56. The circumferential groove 60 may be a single groove that extends continuously about the inner circumference of the mating cavity 44. Alternatively, as one of ordinary skill in the art will appreciate, the circumferential groove 60 may be comprise two or more non-continuous groove segments (not shown).

The knobs 56, axial slots 58 and circumferential groove 60 cooperate to form locking mechanism for the prosthesis system 10. This locking mechanism allows rotation of the tibial bearing insert 12 with respect to the tibial tray by travel of the knobs 56 within groove 60. Simultaneously, the circumferential groove 60 provides positive axial securement of the tibial bearing insert 12 within the tibial tray 14 when the tibial bearing insert is properly mounted within the tibial tray. This is accomplished by engaging the positive surface features (i.e., knobs 56) of the tibial bearing insert 12 within one of the negative surface features (i.e., circumferential groove 60) of the mating cavity. As noted above, the knobs 56 are preferably non-deformable and the relative dimensions of the knobs 56 and groove 60 are such that the knobs 56 are engaged within the groove 60 and cannot be removed from groove 60 except through axial slot 58.

Circumferential groove 60 preferably is formed as a recess within interior side wall 45 of cavity 44. As such, circumferential groove 60 includes a proximal shoulder 61 or another suitable structure that is effective to maintain the knobs 56 within groove 60.

As shown in FIGS. 10 through 14, other embodiments of the invention allow the knobs 56 to be disposed at proximal and intermediate portions of the mating stem rather than at a distal end as in the embodiment shown in FIGS. 1 through 9. One of ordinary skill in the art will readily appreciate that only minor modifications to this prosthesis system need be made to accommodate the proximal placement of the knobs. For example, the axial slot 58 will have a shorter length than the embodiments shown in FIGS. 1 through 9. Moreover, the circumferentially groove 60 will be placed immediately distally of the axial slots 58 and at a more proximal location on the mating cavity.

Figure 15:
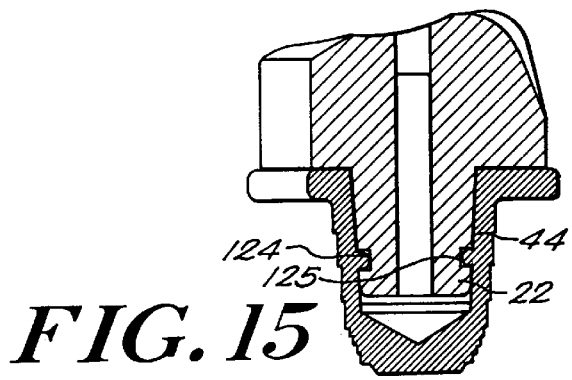
FIG. 15 is a sectional view of an alternative embodiment of a tibial component of a knee joint prosthesis system.

FIG. 15 shows an alternative embodiment, similar to what is described above, except that a positive surface feature 124 is formed within mating cavity 44 and a negative surface feature 125 is formed on mating stem 22.

The prosthesis system 10 may be assembled as follows. Assuming that the placement of positive and negative surface features is a shown in FIGS. 1–14, the tibial bearing insert 12 is oriented such that the anterior and posterior surfaces 13, 15 thereof are offset approximately 90° from the anterior and posterior surfaces 17, 19 of the tibial tray. This enables the knobs 56 to be disposed within axial slots 58 of the mating cavity 44. Further, this orientation allows the mating stem 22 of the tibial bearing insert 12 to be inserted within the mating cavity 44. Once the mating stem 22 is fully inserted, the knobs 56 extend beyond the distal end of the axially oriented slots 58 and communicate with the circumferential groove 60. At this point, the tibial bearing insert can be rotated into its proper position in which the posterior and anterior sides of the tibial bearing insert and the tibial tray are aligned with one another.

When properly installed, the tibial bearing insert and the tibial tray are axially secured to one another. That is, the engagement of the knobs 56 within the circumferential groove 60 prevents axial separation of the components. Generally, the axially secured tibial bearing insert can withdstand an upwardly directed axial force of at least about 1 kg, and more preferably from about 14 kg to about 90 kg. The relative dimensions of the circumferential groove 60 and knob 56 should be such that a clearance fit is achieved. That is, the tibial tray should be free to rotate with little or no friction, but substantially no vertical movement of the tibial bearing insert 12 relative to the tibial tray 24 should exist when the knobs 56 are engaged by circumferential groove 60 and misaligned with slot 58.

One of ordinary skill in the art will appreciate that the components of the system 10 of the invention can be made from a variety of known materials. The tibial bearing insert typically is made from a polymeric material, such as ultra high molecular weight polyethylene. The tibial bearing insert can be made of a variety of known metals and metal alloys that are suitable for implantable prostheses.

One of ordinary skill in the art will further appreciate that minor modifications may be made to the invention described herein without departing from its intended scope. All references noted herein are expressly incorporated by reference in their entirety.

What is claimed is:

1. A joint prosthesis system, comprising:
   a first component having a superior mounting surface and an inferior bone-contacting surface, the bone-contacting surface including an anchor stem having outer, implantable side and distal walls and interior side and distal walls;
   a cavity formed in the superior mounting surface and extending into the anchor stem, the cavity being defined by the interior side and distal walls of the anchor stem;
   a second component, having a superior articulation surface and an inferior surface mountable upon the mounting surface of the first component, the inferior surface including an elongate mating stem having a length that is greater than a diameter, the elongate mating stem being integrally formed with the second component of the same material from which the second component is formed, the mating stem being mountable within the cavity and having a shape and a size complementary to the cavity; and
   a selectively engagable locking mechanism including at least one non-deformable positive surface feature on one of the mating stem and the cavity and at least one cooperating negative surface feature on the other of the mating stem and the cavity, the locking mechanism being effective, when engaged, to permit rotation of the second component relative to the first component and to provide positive axial securement of the second component to the first component.

2. The system of claim 1 wherein the first component is a tibial tray and the second component is a tibial bearing insert.

3. The system of claim 2, further comprising:
   an axial bore formed in the superior surface of the tibial bearing insert and extending into the mating stem; and
   a reinforcement pin mountable within the axial bore in a frictional fit such that a proximal portion of the reinforcement pin does not protrude from the superior surface of the tibial bearing insert.

4. The system of claim 1 wherein the at least one positive surface feature is formed on an exterior side wall of the mating stem and the at least one negative surface feature is disposed on the interior side wall of the cavity.

5. The system of claim 4 wherein two positive surface features are disposed opposite one another on the exterior side wall of the mating stem.

6. The system of claim 4 wherein the locking mechanism comprises:
   at least one axial slot formed in the interior side wall of the cavity;
   a circumferential groove formed in the cavity distally of and in communication with the axial slot;
   at least one positive surface feature protruding from the exterior side wall of the mating stem, the positive surface feature having dimensions sufficient to permit the mating stem to fit within the cavity only when the positive surface feature is aligned with the axial slot.

7. The system of claim 6 wherein the circumferential groove is positioned to receive the positive surface feature upon full insertion of the mating stem within the cavity.

8. The system of claim 7 wherein the circumferential groove includes at a proximal end thereof a structure that is effective to prevent removal of the mating stem from the cavity when the positive surface feature is not in alignment within the axial slot.

9. The system of claim 1 wherein the mating stem is an elongate member.

10. The system of claim 9 wherein the mating stem has a length in the range of about 4 to 75 mm.

11. The system of claim 10 wherein the cavity has a depth in the range of about 5 to 75 mm.

12. The system of claim 1 wherein the cavity has a nominal diameter that tapers from a largest nominal diameter at a proximal portion of the cavity to a smallest nominal diameter at a distal portion of the cavity.

13. The system of claim 12 wherein the nominal diameter of the cavity tapers at an angle in the range of about 0.25 to 5°.

14. The system of claim 12 wherein the mating stem has a nominal diameter that tapers from a largest nominal diameter at a proximal portion of the mating stem to a smallest nominal diameter at a distal portion of the stem.

15. The system of claim 14 wherein the shape and the nominal diameters of the mating stem and the cavity are complementary to one another.

16. The system of claim 4 wherein the at least one positive surface feature is disposed on the exterior side wall of the mating stem at a location selected from the group consisting of a proximal portion of the mating stem, a distal portion of the mating stem and a portion of the mating stem intermediate the proximal and distal portions thereof.

17. A joint prosthesis, comprising:
   a first component having a superior mounting surface and an inferior bone-contacting surface, the bone-contacting surface including an elongate anchor stem having outer, implantable side and distal walls and interior side and distal walls;
   a cavity formed in the superior mounting surface and extending into the anchor stem, the cavity being defined by the interior side and distal walls of the anchor stem;
   a second component, having a superior articulation surface and an inferior surface mountable upon the mounting surface of the first component, the inferior surface including an elongate mating stem having a length that is greater than a diameter, the elongate mating stem being integrally formed with the second component of the same material from which the second component is formed, the mating stem being mountable within the cavity and having a shape complementary to the cavity; and
   cooperating non-deformable locking means, integrally formed on the mating stem and the cavity, for providing selective axial securement of the mating stem within the cavity while allowing rotation of the second component relative to the first component in the transverse plane.

18. The system of claim 17 wherein the locking means is a bayonet-type locking mechanism having at least one male locking component formed on an exterior wall of the mating stem and at least one female locking component formed on the cavity.

19. The system of claim 17 wherein the first component is a tibial tray and the second component is a tibial bearing insert.

20. The system of claim 19, further comprising:

an axial bore formed in the superior surface of the tibial bearing insert and extending into the mating stem; and a reinforcement pin mountable within the axial bore in a frictional fit such that a proximal portion of the reinforcement pin does not protrude from the superior surface of the tibial bearing insert.

21. A joint prosthesis, comprising:

a first component having a superior mounting surface and an inferior bone-contacting surface, the bone-contacting surface including an elongate anchor stem having outer, implantable side and distal walls and interior side and distal walls;

a cavity formed in the superior mounting surface and extending into the anchor stem, the cavity being defined by the interior side and the distal walls of the anchor stem;

a second component, having a superior articulation surface and an inferior surface rotatably mounted upon the mounting surface of the first component, the inferior surface including an elongate mating stem having a length that is greater than a diameter, the elongate mating stem being integrally formed with the second component of the same material from which the second component is formed, the mating stem being rotatably mounted within the cavity and having a shape and a size complementary to the cavity; and a locking mechanism including at least one non-deformable positive surface feature on the mating stem and at least one cooperating negative surface feature on the cavity, the locking mechanism being effective, when engaged, to permit axial rotation in the medial-lateral plane of the second component relative to the first component and to provide positive axial securement of the second component to the first component.

22. The joint prosthesis of claim 21, wherein the first component is a tibial tray and the second component is a tibial bearing insert.

* * * * *